United States Patent [19]

Henry

[11] Patent Number: 5,366,735
[45] Date of Patent: Nov. 22, 1994

[54] METHOD AND COMPOSITION FOR POST-SURGICAL ADHESION REDUCTION

[75] Inventor: Raymond L. Henry, Grosse Pointe Woods, Mich.

[73] Assignee: Mediventures, Inc., Dearborn, Mich.

[21] Appl. No.: 977,483

[22] Filed: Nov. 17, 1992

Related U.S. Application Data

[60] Division of Ser. No. 517,283, May 1, 1990, abandoned, which is a continuation-in-part of Ser. No. 449,215, Dec. 12, 1989, Pat. No. 5,135,751, which is a division of Ser. No. 272,199, Nov. 16, 1988, Pat. No. 4,911,926.

[51] Int. Cl.⁵ .................. A61K 9/08; A61K 31/74; A61K 9/10
[52] U.S. Cl. .................. 424/426; 424/78.06; 424/423; 424/428; 514/772.1; 514/937; 514/944
[58] Field of Search ............. 424/426, 423, 78.06, 424/428

[56] References Cited

U.S. PATENT DOCUMENTS

| | | | |
|---|---|---|---|
| 2,674,619 | 4/1954 | Lundsted | 260/480 |
| 2,677,700 | 5/1954 | Jackson | 260/488 |
| 2,979,528 | 4/1961 | Lundsted | 260/584 |
| 3,036,118 | 5/1962 | Jackson | 260/484 |
| 3,535,307 | 10/1970 | Moss | 260/209 |
| 3,590,125 | 6/1971 | Hymes | 424/78 |
| 3,639,575 | 2/1972 | Schmolka | 424/78 |
| 3,740,421 | 6/1973 | Schmolka | 424/65 |
| 3,829,506 | 8/1974 | Schmolka | 260/615 B |
| 3,867,521 | 2/1975 | Miskel | 424/37 |
| 3,867,533 | 2/1975 | Schmolka | 424/258 |
| 4,076,799 | 2/1978 | Willer | 424/45 |
| 4,188,373 | 2/1980 | Krezanoski | 424/78 |
| 4,439,196 | 3/1984 | Higuchi | 604/890 |
| 4,465,663 | 8/1984 | Schmolka | 424/78 |
| 4,474,751 | 10/1984 | Haslam | 424/78 |
| 4,474,752 | 10/1984 | Haslam | 424/78 |
| 4,474,753 | 10/1984 | Haslam | 424/78 |
| 4,478,822 | 10/1984 | Haslam | 424/78 |
| 4,495,168 | 1/1985 | Schmolka | 424/45 |
| 4,495,169 | 1/1985 | Schmolka | 424/47 |
| 4,511,563 | 4/1985 | Schmolka | 514/162 |
| 4,540,407 | 9/1985 | Dunn | 604/292 |
| 4,767,619 | 8/1988 | Murray | 424/78 |
| 4,810,503 | 3/1989 | Carson et al. | 424/76.3 |
| 4,861,760 | 8/1989 | Mazuel | 514/54 |
| 4,879,109 | 11/1989 | Hunter | 424/83 |
| 4,883,660 | 11/1989 | Blackman | 424/78 |
| 4,889,722 | 12/1989 | Sheffield | 424/78 |
| 5,068,225 | 11/1991 | Pennell et al. | 514/781 |
| 5,071,644 | 12/1991 | Viegas | 514/772 |
| 5,077,033 | 12/1991 | Viegas | 514/668 |
| 5,124,151 | 6/1992 | Viegas | 424/422 |
| 5,126,141 | 6/1992 | Henry | 424/426 |
| 5,143,731 | 9/1992 | Viegas | 424/486 |

OTHER PUBLICATIONS

Ellis, "The Cause and Prevention of Post Operative Intraperitoneal Adhesions", *Surgery, Gynecology & Obstetrics*, vol. 133, p. 497 (Sep. 1971).

Linsky et al., "Adhesion Reduction in the Rabbit Uterine Horn Model Using an Absorbable Barrier, TC-7", *The Journal of Reproductive Medicine*, vol. 32, 17-20 (1987).

Schmolka, I. R., "Artificial Skin I Preparation and Properties of PLURONIC® F-127 Gels for Treatment of Burns", *Journal of Biomedical Material Research*, vol. 6, 571 (1972).

Smith et al., "Pluronic F-68 Reduces the Endothelial Adherence and Improves the Rheology of Liganded Sickle Erythrocytes", *Blood*, vol. 69, No. 6, pp. 1631-1636 (1987).

Hunter et al., "The Adjuvant Activity of Nonionic Block Polymers Surfactants", *Journal of Immunology*, vol. 127, No. 3 (1981).

*Primary Examiner*—Thurman K. Page
*Assistant Examiner*—James M. Spear
*Attorney, Agent, or Firm*—Dykema Gossett

[57] ABSTRACT

A process and compositions for reducing post-surgical adhesion formation/reformation in mammals following injury to organs situated in mammalian body spaces. Aqueous, isotonic gel compositions, preferably at mammalian body fluid pH, comprising a polyoxyalkylene polymer are applied to injured areas of the organs situated in body cavities such as, the peritoneal, pelvic, or pleural cavity.

31 Claims, No Drawings

METHOD AND COMPOSITION FOR POST-SURGICAL ADHESION REDUCTION

"This application is a divisional of Ser. No. 07/517,283, filed May 1, 1990, now abandoned which was a continuation-in-part of Ser. No. 07/449,215 filed Dec. 12, 1989, now U.S. Pat. No. 5,135,751, which was a divisional of Ser. No. 07/272,199 filed Nov. 16, 1988, now U.S. Pat. No. 4,911,926."

BACKGROUND OF THE INVENTION

1. Field of the Invention

This invention relates to methods and compositions for reducing post-surgical adhesions in the mammalian abdominal or thoracic cavity or other body spaces, whether accidentally or surgically created.

2. Description of the Prior Art

There is a need for a method and composition suitable for use in preventing adhesion formation/reformation in mammals following injury to the organs of the peritoneal, pelvic or pleural cavity, or other body spaces, such as subdural, extraocular, intraocular, otic, synovial, tendon sheath, whether accidentally or surgically created.

According to Ellis in a review entitled "The Cause And Prevention Of Post-operative Intraperitoneal Adhesions" in *Surgery, Gynecology and Obstetrics* for September 1971, volume 133, pages 497–509, at pages 502–503, the prevention of adhesions has been the subject of an enormous amount of work since the beginning of this century. According to Ellis, these attempts have included means of preventing the fibrin-coated walls of the intestine from reaching each other by distending the abdomen with oxygen or filling the abdomen with saline solution, paraffin, olive oil, lanolin, concentrated dextrose solution, macromolecular solutions of all sorts, and silicones.

Menzies and Ellis in an article entitled "Intestinal Obstruction from Adhesions—How Big is the Problem?" *Annals of the Royal College of Surgeons of England*, volume 72, pages 60–63, 1990 reported adhesions findings in 10.4% of 115 patients with first-time laparotomies while 93% of 210 patients had intra-abdominal adhesions due to previous surgery. Admission for intestinal obstruction was made for 0.9% of 28,297 general surgery patients while 3.3% of 4,502 laparotomy patients were admitted for adhesive obstruction. These data emphasize the magnitude of readhesion after adhesiolysis or from subsequent surgical procedures. The authors state on p. 62, that there is currently no effective treatment that prevents their recurrence.

Caspi, Halperin, and Bukovsky in an article entitled "The Importance of Periadnexal Adhesions in Reconstructive Surgery for Infertility" appearing in *Fertility and Sterility* for Mar. 1982, volume 31, number 3, pages 296–300, at page 299 indicate that despite experimental and clinical efforts in the prevention of adhesion formation following surgery, no major advances have thus far been achieved. The authors discuss the use of post-operative intraperitoneal instillation of a mixture of hydrocortisone acetate (a glucocorticoid), promethazine, and ampicillin. As an alternative method of treatment, a low molecular weight dextran (a branched polysaccharide composed of glucose units) was also instilled intraperitoneally in another group of patients. The authors conclude that the intraperitoneal instillation of high doses of glucocorticoids combined with early hydrotubations seems to be a worthwhile method.

Musich and Behrman in an article entitled "Infertility Laparoscopy In Perspective: Review of 500 Cases" appearing in *The American Journal of Obstetrics and Gynecology* for Jun. 1, 1982, pages 293–303, at page 300 in the discussion section of the article disclose that there is a need to prevent adhesions subsequent to surgery in view of a study of 35 patients which indicated that 30 of these patients having previous tuboplasties had severe adhesions, one-third of which were judged to be inoperable.

High molecular weight dextran either alone or in combination with dextrose has been used in the prevention of peritoneal adhesions subsequent to surgery. Dextran is clinically standardized to a low molecular weight of about 75,000 by partial hydrolysis and fractional precipitation of the high molecular weight particles which normally have molecular weights of up to 200,000. Dextran is a polymer of glucose which has a chain-like structure and is produced from sucrose by Leuconostoc bacteria. In articles appearing in *Fertility and Sterility*, volume 33, number 6, June 1980, pages 660–662, Holtz, Baker, and Tsai and volume 34, number 4, October 1980, pages 394–395, by Holtz and Baker, results are reported of the adhesion reducing effects of a 32% (aqueous) solution of dextran 70 containing 10% dextrose (sold under the trade name HYSKON by Pharmacia, of Piscataway, N.J.). Holtz et al postulate several mechanisms of action in the prevention of peritoneal adhesions utilizing HYSKON including a simple mechanical separation of adjacent surfaces, termed a hydroflotation effect.

Project coordinator diZerega and several contributors have reported the results of a large study in an article entitled "Reduction of Post-operative Pelvic Adhesions with Intraperitoneal 32% Dextran 70: A Prospective, Randomized Clinical Trial" in *Fertility and Sterility*, volume 40, number 5, for November 1983, pages 612–619. The authors, at page 618, indicate that the use of Dextran intraperitoneally has limitations such as the reported tendency of HYSKON to support bacterial proliferation and concern over the anaphylactoid potential of dextran. In addition, the benefit of Dextran 70 in preventing post-operative adhesions was shown to be limited to the more dependent regions of the pelvis.

Borten, Seibert, and Taymor in *Obstetrics and Gynecology*, volume 61, number 6, June 1983, pages 755–757 report in an article entitled "Recurrent Anaphylactic Reaction to Intraperitoneal Dextran 75 Used for Prevention of Postsurgical Adhesions". These authors indicate that anaphylactic reaction to Dextran administered intravenously is well documented and report such a reaction after intraperitoneal administration of Dextran.

Linsky in *The Journal of Reproductive Medicine* for Jan. 1987, pages 17–20 in an article entitled "Adhesion Reduction in the Rabbit Uterine Horn Model Using an Absorbable Barrier, TC-7". These authors report that the use of a resorbable fabric barrier provides a significant reduction in post-operative adhesion formation and that no gross remnants of the fabric barrier material were noted, subsequent to initial placement, after a two week period.

Oelsner et al in *The Journal of Reproductive Medicine* for November 1987, volume 32, number 11, pages 812–814, report results of a comparison of sodium carboxymethyl cellulose, 32% dextran 70, and chondroitin sulfate to prevent the formation of postoperative adhesions in the rabbit uterus. The authors report superior results with chondroitin sulfate which is described as a member of a family of biochemical compounds referred to as glycosaminoglycans (formerly termed mucopolysaccharides), to which hyaluronic acid, heparitin sulfate and heparin also belong.

Peterson et al in *The Journal of Hand Surgery* for Jan. 1990, volume 15A, number 1, pages 48–56 state on page 48 that despite refinements in surgical technique and improved postoperative rehabilitation programs, results (of repair of lacerated flexor tendons) are often unsatisfactory because of the formation of adhesions around the repair site which restrict tendon gliding and prevent flexion of the digit. The authors on page 49 refer to use of biological barriers including paratenon, endothelial vein grafts, arterial grafts, fascial sheath grafts, and synthetic materials such as, metal tubes, cellophane, celloidin, polytef (Teflon), polyethylene, millipore cellulose tubes, and silcone sheeting. Complications from use of these materials included severe inflammatory response, ingrowth of adhesions around the edges of the material, and prevention of nutrient diffusion leading to tendon necrosis. They conclude that a suitable biologic or synthetic flexor sheath patch has not yet gained widespread clinical acceptance. The authors tested primary tendon sheath repair, autogenous fascia lata patches, and a synthetic patch of expanded polytetraflorethylene surgical membranes. They concluded on p. 55 that restoration of the sheath integrity was beneficial in reducing adhesion formation, but it is not possible to advocate one particular method.

The use of ethylene oxide/propylene oxide block copolymers as surfactants for use in surgical scrub solutions and the topical application of 10% solutions of these copolymers to wounds is described in Edlich et al in the *Journal of Surgical Research*, volume 14, number 4, April 1973, pages 277–284. The test results indicate that the copolymers having an ethylene oxide:propylene oxide ratio of 4:1 provide less inflammatory response in a wound to which the copolymer is applied in comparison with a copolymer having an ethylene oxide:propylene oxide ratio of 1:4. There is no indication in Edlich et al or any cited prior art that such copolymers are useful in reducing post-operative adhesions or that isotonic, aqueous solutions of such copolymers are useful in reducing post-operative adhesions.

Over the years, methods have been developed to achieve the efficient delivery of a therapeutic drug to a mammalian body part requiring pharmaceutical treatment. Use of an aqueous liquid which can be applied at room temperature as a liquid but which forms a semisolid gel when warmed to body temperature has been utilized as a vehicle for drug delivery since such a system combines ease of application with greater retention at the site requiring treatment than would be the case if the aqueous composition were not converted to a gel as it is warmed to mammalian body temperature. In U.S. Pat. No. 4,188,373, PLURONIC ® polyols are used in aqueous compositions to provide thermally gelling aqueous systems. Adjusting the concentration of the polymer provides the desired sol-gel transition temperature, that is, the lower the concentration of polymer, the higher the sol-gel transition temperature.

In U.S. Pat. Nos. 4,474,751; '752; '753; and 4,478,822 drug delivery systems are described which utilize thermosetting polyoxyalkylene gels; the unique feature of these systems is that both the gel transition temperature and/or the rigidity of the gel can be modified by adjustment of the pH and/or the ionic strength, as well as by the concentration of the polymer.

Other patents disclosing pharmaceutical compositions which rely upon an aqueous gel composition as a vehicle for the application of the drug or cosmetic preparation are U.S. Pat. Nos. 4,883,660; 4,861,760; 4,810,503; 4,767,619; and 4,511,563.

While the prior art is silent with respect to the use of aqueous drug delivery vehicles which are isotonic to mammalian bodily fluids, osmotic drug delivery systems are disclosed in U.S. Pat. No. 4,439,196 which utilize a multi-chamber compartment for holding osmotic agents, adjuvants, enzymes, drugs, pro-drugs, pesticides, and the like. These materials are enclosed by semipermeable membranes so as to allow the fluids within the chambers to diffuse into the environment into which the osmotic drug delivery system is in contact. The drug delivery device can be sized for oral ingestion, implantation, rectal, vaginal, or ocular insertion for delivery of a drug or other beneficial substance. Since this drug delivery device relies on the permeability of the semipermeable membranes to control the rate of delivery of the drug, the drugs or other pharmaceutical preparations, by definition, are not isotonic with mammalian blood.

SUMMARY OF THE INVENTION

Polyoxyalkylene compositions and a process are disclosed for reducing post-surgical adhesion formation/reformation in mammals following injury to the organs of the peritoneal, pelvic or pleural cavity. The compositions of the invention are also useful to reduce adhesion formation/reformation in other body spaces such as the subdural, extraocular, intraocular, otic, synovial, tendon sheath, or those body spaces created either surgically or accidentally. Compositions comprising a polymer capable of forming an aqueous gel are useful. The useful compositions comprise (1) a combination of a polyether and a surfactant or (2) a polyoxyalkylene block copolymer. Polyphase systems are also useful and may contain non-aqueous solutes, non-aqueous solvents, and other non-aqueous additives. Homogeneous, polyphase systems can contain such additives as water insoluble high molecular weight fatty acids and alcohols, fixed oils, volatile oils and waxes, mono-, di-, and triglycerides, and synthetic, water insoluble polymers without altering the functionality of the system. In one embodiment of the invention, the concentration of the block copolymer in the compositions of the invention can be adjusted to take advantage of the gelation properties of certain polyoxyalkylene block copolymers. For instance, at certain concentrations aqueous solutions of said block copolymers form clear gels at mammalian body temperatures but are liquids at ambient temperatures. The aqueous solutions of said block copolymers can be provided as isotonic and pH balanced compositions which match the pH and osmotic pressure of mammalian bodily fluids. Subsequent to deposition of the compositions of the invention in the peritoneal, pelvic, or pleural cavity of a mammal, or other body spaces, as described above, the polyoxyalkylene block copolymer is absorbed by the tissues with which it is in contact and the block copolymer is eventually excreted in a non-metabolized form, mainly in the urine. In another embodiment of the invention, aqueous gels are produced by combination of an alpha-olefin epoxide capped polyether and a surfactant, as described in U.S. Pat. No. 4,810,503. In this embodiment, the aqueous, isotonic gels are applied as gels to injured tissues in the peritoneal, pelvic, or pleural cavities or other body spaces to reduce post-surgical adhesion formation/reformation.

In addition to functioning as a means of reducing post-operative adhesion formation/reformation in mammals following surgical or accidental injury to the peritoneal, pelvic or pleural cavity or other body spaces, the polyoxyalkylene compositions provide an isotonic environment surrounding the surgical injury which reduces adhesion formation/reformation. For instance, the polyoxyalkylene block copolymer can be instilled within the uterine cavity as a distending medium during diagnostic or operative intrauterine endoscopic procedures. This procedure has two advantages. First, since certain aqueous concentrations of the preferred polyoxyalkylene block copolymers form a clear gel, their use is well suited for visualization of the uterine cavity. Second, since these aqueous solutions are liquids at room temperature and below and form a clear gel at body temperature, the use of said solutions to separate the uterine cavity walls will diminish or prevent post-surgical adhesion formation. Similarly, the application of the aqueous, capped, polyoxyalkylene, polyether-surfactant combination as gels provides a similar adhesion reducing effect.

Optionally, the polyoxyalkylene block copolymer or capped polyether-surfactant gels can be utilized advantageously in combination with bacteriostatic or bactericidal agents, fibrinolytic agents, and agents effective in preventing leucocyte migration into the area of surgical injury.

DETAILED DESCRIPTION OF THE INVENTION

A process and compositions are disclosed for reducing post-operative adhesion formation/reformation in mammals following surgical or accidental injury to the organs of the peritoneal or pleural cavity or other body spaces. In this specification and claims, the terms "peritoneal" and "abdominal" cavity are used as synonyms, as are the terms "pleural" and "thoracic" cavity. The compositions can include at least one of a bacteriostatic or bactericidal agent, an agent effective in preventing leucocyte migration into the area of surgical injury, and a fibrinolytic agent.

In one embodiment of the invention, the preferred aqueous, polyoxyalkylene block copolymer compositions are prepared at concentrations so as to take advantage of the gelation properties of certain of said block copolymers and at a pH and osmotic pressure which match that of bodily fluids (pH 7.4 and 290 mOsm/kg). When certain of the polyoxyalkylene block copolymers of the invention are present in aqueous solutions at concentrations preferably of about 15% to about 30% by weight, such compositions can provide liquid compositions at ambient temperatures or below which revert to gel compositions upon contact with living mammalian tissue.

Alternatively, useful compositions of the invention include aqueous compositions comprising at least one polyoxyalkylene block copolymer which does not form gels at mammalian body temperature as well as aqueous, isotonic, polyoxyalkylene gel polymers comprising an alpha olefin epoxide capped polyether and a surfactant. It is believed that the aqueous compositions of the invention which do not form gels upon contact with living mammalian tissue as well as those which are applied to mammalian tissue in the gel state, also function to prevent the formation/reformation of adhesions subsequent to surgical injury by a mechanism of action which has been termed in the prior art "hydroflotation". Thus the injured tissues are prevented from contacting adjacent tissues by the means of the inclusion of a foreign fluid or gel in the peritoneal, pelvic, or pleural cavity or other body spaces. It is believed that the mechanism of action to prevent the formation/reformation of adhesions is, in addition to hydroflotation, properly characterized as the result of separating the adjacent mammalian tissues by a firm, adherent gel coating.

The polyoxyalkylene block copolymer compositions of one embodiment of the invention include at least one block copolymer as below defined, optionally in combination with at least one of an adjuvant such as a humectant, a bactericide, a bacteriostatic agent, an antihistamine, or a decongestant, an agent to prevent leucocyte migration into the area of surgical injury, or a fibrinolytic agent. The copolymer is applied to injured tissue in a major amount in combination with a minor amount of said adjuvant. Useful humectants include, but are not limited to glycerin, propylene glycol, and sorbitol. Useful bactericides which can be administered in admixture with the aqueous compositions of the invention include antibacterial substances such as β-lactam antibiotics, such as cefoxitin, n-formamidoyl thienamycin and other thienamycin derivatives, tetracyclines, chloramphenicol, neomycin, gramicidin, bacitracin, sulfonamides; aminoglycoside antibiotics such as gentamycin, kanamycin, amikacin, sisomicin and tobramycin; nalidixic acids and analogs such as norfloxacin and the antimicrobial combination of fluoroalanine/pentizidone; nitrofurazones, and the like. Antihistamines and decongestants such as pyrilamine, chlorpheniramine, tetrahydrozoline, antazoline, and the like, can also be used in admixtures as well as anti-inflammatories such as cortisone, hydrocortisone, beta-methasone, dexamethasone, fluocortolone, prednisolone, triamcinolone, indomethacin, sulindac, its salts and its corresponding sulfide, and the like.

Useful leucocyte migration preventing agents which can be used in admixtures include but are not limited to silver sulfadiazine, acetylsalicylic acid, indomethacin, and Nafazatrom. Useful fibrinolytic agents include urokinase, streptokinase, tissue plasminogen activator (TPA), and acylated plasmin. The block copolymer compositions of the invention comprise: at least one polyoxyalkylene block copolymer of the formula $$Y[(A)_{\overline{n}}-E-H]_x \qquad (I)$$

wherein A is a polyoxyalkylene moiety having an oxygen/carbon atom ratio of less than 0.5, x is at least 2, Y is derived from water or an organic compound containing x reactive hydrogen atoms, E is a polyoxyalkylene moiety constituting at least about 60% by weight of the copolymer, n has a value such that the average molecular weight of A is at least about 500 to about 900, as determined by the hydroxyl number of a hydrophobe base intermediate, $$Y[(A)_{\overline{n}}-H]_x \qquad (II)$$

and the total average molecular weight of the copolymer is at least about 5000.

In addition to those polyoxyalkylene polymers described above, which are suitable in the formation of the pharmaceutical compositions of the invention, other polyoxyalkylene polymers which form gels at low concentrations in water are suitable. These are described in U.S. Pat. No. 4,810,503, incorporated herein by reference. These polymers are prepared by capping conventional polyoxyalkylene polyether polyols with an alpha-olefin epoxide having an average of about 20 to about 45 carbon atoms, or mixtures thereof. Aqueous solutions of these polymers gel in combination with surfactants, which can be ionic or nonionic. The combination of the capped polyether polymers and the surfactants provide aqueous gels at low concentrations of the capped polymer and surfactant which generally do not exceed 10% by weight total. Detailed methods of preparing these aqueous gels are disclosed in U.S. Pat. No. 4,810,503. Preparation of said aqueous gels is generally described below. Preferred surfactants for use in preparing these gels are also disclosed in said patent.

A conventional copolymer polyether polyol is prepared by preparing block or heteric intermediate polymers of ethylene oxide and at least one lower alkylene oxide having 3 to 4 carbon atoms as intermediates. These are then capped with the alpha-olefin epoxide to prepare the polymers of this invention. Ethylene oxide homopolymers capped with said alpha-olefin oxides are also useful as intermediates.

The hereric copolymer intermediate is prepared by mixing ethylene oxide and at least one lower alkylene oxide having 3 to 4 carbon atoms with a low molecular weight active hydrogen-containing compound initiator having at least two active hydrogens and preferably, 2 to 6 active hydrogen atoms such as a polyhydric alcohol, containing from 2 to 10 carbon atoms and from 2 to 6 hydroxyl groups, heating said mixture to a temperature in the range of about 50° C. to 150° C., preferably, from 80° C. to 130°, under an inert gas pressure, preferably, from about 30 psig to 90 psig.

A block copolymer intermediate is prepared by reacting either the ethylene oxide or said alkylene oxide having 3 to 4 carbon atoms with said active hydrogen-containing compound followed by reaction with the other alkylene oxide.

The ethylene oxide and the alkylene oxides having from 3 to 4 carbon atoms are used in said intermediates in amounts so that the resulting polyether product will contain at least 10 percent by weight, preferably about 70 percent to about 90 percent by weight, ethylene oxide residue. The ethylene oxide homopolymer intermediate is prepared by reacting ethylene oxide with said active hydrogen-containing compound. The reaction conditions for preparing the block copolymer and ethylene oxide homopolymer intermediates are similar to those for the heretic copolymer intermediate. The temperature and pressure are maintained in the above ranges for a period of about one hour to ten hours, preferably one to three hours.

The alpha-olefin oxides which are utilized to modify the conventional polyether intermediate of the prior art are those oxides and the commercially available mixtures thereof generally containing an average of about 20 to 45, preferably about 20 to 30, carbon atoms. The amount of alpha-olefin required to obtain the more efficient capped polyethers is generally about 0.3 to 10 percent, preferably about 4 to 8 percent, of the total weight of the polyethers of the invention.

Since the preparation of heteric and block copolymers of alkylene oxides and ethylene oxide homopolymers are well known in the art, further description of the preparation of said polymers is unnecessary. Further details of the preparation of heteric copolymers of lower alkylene oxide can be obtained in U.S. Pat. No. 3,829,506, incorporated herein by reference. Further information on the preparation of block copolymers of lower alkylene oxides can be obtained in U.S. Pat. Nos. 3,535,307; 3,036,118; 2,979,578; 2,677,700; and 2,675,619 incorporated herein by reference.

The surfactants may be ionic or non-ionic and many surfactants and types of surfactants may be employed. While all surfactants may not be effective in the preparation of the isotonic gels of the instant invention, the fact that many are effective makes it a simple matter for one skilled in the art to select such surfactant with a minimum of trial and error.

The amounts of capped polyether polymer and surfactant may be as little as 1.0 percent by weight or less of each depending on the type and amount of the other component. There appears to be no maximum amount of either component than that dictated by economic considerations. However, the total amount of capped polymer and surfactant would generally not exceed 10 percent by weight.

Post-operative pelvic adhesions have been associated with infertility. Significant periadnexal adhesions have been found, as reported by Musich and Behrman, as previously cited, upon laparoscopy in 72% of 106 patients having unexplained infertility who had previously undergone various pelvic surgical procedures. Prevention of such adhesions has been proposed in the prior art by treatment with aqueous dextran solutions of low molecular weight. The prior art use of aqueous dextran solutions (i.e., dextran 70 at 32% solids) has shown adverse reactions and little or no reduction of post-operative pelvic adhesions.

In addition, an oxidized cellulose fabric barrier (sold under the trade designation TC-7 by Johnson and Johnson Products, Inc., New Brunswick, N.J.), which is resorbable subsequent to utilization, has been used in the prior art as a treatment to prevent adhesions to the peritoneum by preventing abutting injured organ surfaces from making contact therewith. Chondroitin sulfate solutions have also been proposed for intraperitoneal use in the prevention of adhesions in rabbits. Each of these proposed methods of avoiding post-operative adhesions have disadvantages which are overcome by the method of the present invention.

The mechanism of action of all of these treatments is proposed to be the result of the persistent separation of adjacent surgically injured surfaces thus permitting healing to occur without the formation of fibrinous bands between abutting surfaces which are characterized as adhesions. For instance, upon injury to the peritoneum there results an outpouring of a serosanguinous exudate which is of a proteinaceous nature. This fluid subsequently coagulates, producing fibrinous bands between abutting surfaces that become subsequently organized by fibroblast proliferation to produce collagenous adhesions. This process is thought to be initiated and well advanced within the first three days subsequent to surgical injury.

Preferably, the block copolymers which are useful are selected from those defined above in formula I which contain at least about 60% by weight, preferably at least about 70%, by weight and most preferably at least about 80% by weight of the residue of ethylene oxide (polyoxyethylene moiety). Said copolymers have a total average molecular weight of at least about 5000, and form a gel at mammalian body temperature, when in an aqueous solution at a concentration generally, of about 10 to about 40%, preferably, about 15 to about 30% by weight and most preferably, about 18% to about 25% by weight.

The proportion of water used is about 60% to about 90%, by weight, preferably, about 70% to about 85%, by weight, and most preferably, about 75% to about 82% by weight, based upon the total weight of the composition of the invention. Useful polyoxyalkylene block copolymers which will form gels in such aqueous solutions can be prepared using a hydrophobe base (such as A in Formulas I and II) derived from propylene oxide, butylene oxide, or mixtures thereof. These block copolymers and representative methods of preparation are further generally described in U.S. Pat. Nos. 2,677,700; 2,674,619; and U.S. Pat. No. 2,979,528, incorporated herein by reference.

Generally, the polyoxybutylene-based block copolymers useful in the compositions of the invention are prepared by first condensing 1,2 butylene oxide with a water soluble organic compound initiator containing 1 to about 6 carbon atoms such as 1,4 butylene glycol or propylene glycol and at least 2 reactive hydrogen atoms to prepare a polyoxyalkylene polymer hydrophobe of at least about 500, preferably at least about 1000, most preferably at least about 1500 average molecular weight. Subsequently, the hydrophobe is capped with an ethylene oxide residue. Specific methods for preparing these compounds are described in U.S. Pat. No. 2,828,345 and British Patent No. 722,746, both of which are hereby incorporated by reference.

Useful polyoxybutylene based block copolymers conform to the following generic formula:

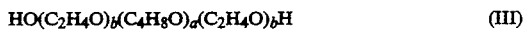
$$HO(C_2H_4O)_b(C_4H_8O)_a(C_2H_4O)_bH \qquad (III)$$

wherein a is an integer such that the hydrophobe base represented by $(C_4H_8O)_a$ has a molecular weight of at least about 500, preferably at least about 1000 and most preferably at least about 3000, as determined by hydroxyl number, the polyoxyethylene chain constituting at least about 60%, preferably at least about 70% by weight of the copolymer, and the copolymer having a total average molecular weight of at least about 5000, preferably at least about 10,000, and, most preferably, at least about 15,000.

The copolymer is characterized in that all the hydrophobic oxybutylene groups are present in chains bonded to an organic radical at the former site of a reactive hydrogen atom thereby constituting a polyoxybutylene base copolymer. The hydrophilic oxyethylene groups are used to cap the polyoxybutylene base polymer.

Polyoxyethylene-polyoxypropylene block copolymers which can be used to form aqueous gels can be represented by the following formula:

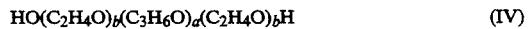
$$HO(C_2H_4O)_b(C_3H_6O)_a(C_2H_4O)_bH \qquad (IV)$$

wherein a is an integer such that the hydrophobe base represented by $(C_3H_6O)$ has a molecular weight of at least about 900, preferably at least about 2500, most preferably at least about 4000 average molecular weight, as determined by hydroxyl number; the polyoxyethylene chain constituting at least about 60%, preferably at least about 70% by weight of the copolymer, and the copolymer having a total average molecular weight of at least about 5000, preferably at least about 10,000, and most preferably at least about 15,000.

Polyoxyethylene-polyoxypropylene block copolymer adducts of ethylenediamine which can be used may be represented by the following formula:

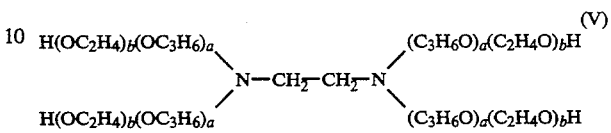

$$(V)$$

wherein a and b are integers such that the copolymer may have (1) a hydrophobe base molecular weight of at least about 2000, preferably at least about 3000, and most preferably at least about 4500, (2) a hydrophile content of at least about 60%, preferably at least about 70% by weight, and (3) a total average molecular weight of at least about 5000, preferably at least about 10,000, and most preferably at least about 15,000.

The hydrophobe base of the copolymer of formula V is prepared by adding propylene oxide for reaction at the site of the four reactive hydrogen atoms on the amine groups of ethylenediamine. An ethylene oxide residue is used to cap the hydrophobe base. These hydrophile polyoxyethylene groups are controlled so as to constitute at least about 60%, preferably at least about 70% by weight, and most preferably at least about 80% by weight of the copolymer.

The procedure used to prepare aqueous solutions which form gels of the polyoxyalkylene block copolymers is well known. Either a hot or cold process for forming the solutions can be used. A cold technique involves the steps of dissolving the polyoxyalkylene block copolymer at a temperature of about 5° to about 10° C. in water. When solution is complete the system is brought to room temperature whereupon it forms a gel. If the hot process of forming the gel is used the polymer is added to water heated to a temperature of about 75° C. to about 85° C. with slow stirring until a clear homogeneous solution is obtained. Upon cooling, a clear gel is formed. Block copolymer gels containing polyoxybutylene hydrophobes must be prepared by the above hot process, since these will not liquify at low temperatures.

As used herein, the term "gel" is defined as a solid or semisolid colloid containing a certain quantity of water. The colloidal solution with water is often called a "hydrosol".

The organic compound initiator which is utilized in the process for the preparation of the polyoxyalkylene block copolymers generally is water or an organic compound and can contain a plurality of reactive hydrogen atoms. Preferably, Y in formulas I and II above is defined as derived from a water soluble organic compound having 1 to about 6 carbon atoms and containing x reactive hydrogen atoms where x has a value generally, of at least 1, preferably, a value of at least 2. Falling within the scope of the compounds from which Y is derived from water soluble organic compounds having at least two reactive hydrogen atoms are water soluble organic compounds such as propylene glycol, glycerin, pentaerythritol, trimethylolpropane, ethylenediamine, and mixtures thereof and the like.

The oxypropylene chains can optionally contain small amounts of at least one of oxyethylene or oxybutylene groups. Oxyethylene chains can optionally contain small amounts of at least one of oxypropylene oxybutylene groups. Oxybutylene chains can optionally contain small amounts of at least one of oxyethylene or oxypropylene groups. The physical form of the polyoxyalkylene block copolymers can be a viscous liquid, a paste, or a solid granular material depending upon the molecular weight of the polymer. Useful polyoxyalkylene block copolymers generally have a total average molecular weight of about 5000 to about 50,000, preferably about 5,000 to about 35,000 and most preferably about 10,000 to about 25,000.

Preferably the polyoxyalkylene block copolymer is applied to surgically injured tissue as an aqueous solution which upon contact with living mammalian tissue forms a firm, adherent gel. Where a polyoxyalkylene block copolymer is a viscous liquid or paste, these compositions can be applied without dilution to areas of surgical injury in the abdominal or thoracic cavities.

The following examples illustrate the various aspects of the invention but are not intended to limit its scope. Where not otherwise specified throughout this specification and claims, temperatures are given in degrees centigrade, and parts, percentages, and proportions are by weight.

EXAMPLE 1

An aqueous solution was made of a polyoxyethylene-polyoxypropylene block copolymer having the structure generically shown as formula IV and having a polyoxypropylene hydrophobe base average molecular weight of about 4000, a total average molecular weight of about 11,500, and containing oxyethylene groups in the amount of about 70% by weight of the total weight of copolymer. This copolymer is sold under the trademark PLURONIC® F-127 by the BASF Corporation, Parsippany, N.J. A solution was made by dissolving said polymer in cold (4° C.) distilled water to give a concentration of 30% by weight in accordance with the cold process described above for forming aqueous solutions. More specific solution procedures are described in "Artificial Skin I Preparation and Properties of Pluronic F-127 Gels for Treatment of Burns", *J. Biomed. Mater. Res.* 6, 527, 1972, incorporated herein by reference. The block copolymer has the formula:

(VI)

This solution is a liquid at 4° C. and forms a gel which is adherent to living tissue upon contact. This solution was applied at 4° C. in the following experiments.

EXAMPLES 2-23

The following test procedure was utilized in order to determine the effect of the solution of Example 1 on surgically injured rats. Twenty-two female Sprague-Dawley rats having a 300–400 gram body weight were anesthetized with pentobarbital sodium (30 milligrams per kilogram of body weight) by application intraperitoneally through the left lumbar region of the ventral abdominal wall. The abdomen was thereafter opened by a 5 centimeter midline vertical incision subsequent to cleansing of the abdominal surface with povidone-iodine solution and removing hair by shaving. A one centimeter segment of each uterine horn was stripped of serosa and an opposing one square centimeter of parietal peritoneum was excised, including the underlying muscle layer. Hemostasis was not attained.

Subsequently, the block copolymer solution of Example 1 was applied at a temperature of 4° C. to both the surgically injured area of the uterine horn and the parietal peritoneum surgical injury but only on one side of the abdomen. After the first application had formed a gel, a second layer of block copolymer solution was applied. Approximately 0.5 to 1.5 cubic centimeters of the block copolymer solution was applied depending upon the amount necessary to adequately cover (on one side of the abdomen) both the surgically injured one centimeter sediment of the uterine horn and the surgically injured one square centimeter area of parietal peritoneal tissue.

The remaining side of the abdomen which was surgically injured in the same manner was left untreated. The portion of the uterine horn which was stripped of serosa was then attached within 0.5 centimeter of the surgical injury to the peritoneal parietal area by a single 3-0 VICRYL ligature suture. This was done to insure that the injured surface of the uterine horn remained in close proximity to the surgical injury of the parietal area of the peritoneum until re-peritonealization had occurred. The abdominal wall was closed with a single layer of interrupted 0—0 VICRYL suture and 21 days later each animal was sacrificed and the abdomen was examined for the presence of adhesions.

The following grading system was used to evaluate the results obtained:
0=no adhesions observed.
1=adhesions on 25% of the surgically injured area.
2=adhesions on 50% of the surgically injured area.
3=adhesions on 100% of the surgically injured area.

The tenacity of the adhesion which formed was evaluated according to the following grading system:
0.0=no resistance to separation.
0.5=moderate force of separation required to rupture the adhesion.
1.0=strong force or cutting necessary for separation.

A rating for the results obtained was obtained by adding the results in each of the grading systems. Results therefore would range from 0.0 to 4.0 for each surgically injured area evaluated. The data were analyzed by a rank sum test and also by analysis of variance.

Since the bilaterally surgically injured areas of each rat were treated with block copolymer solution only unilaterally, each rat served as its own control. Twenty of the 22 rats used in the evaluation survived a 21 day period prior to sacrifice. Two animals died from failure to adequately close the abdominal incision to seal the peritoneal cavity and its contents.

Nineteen of the 20 surviving animals developed adhesions on the untreated control side of the abdomen. The combined score for the untreated control, including area and tenacity of the adhesions, averaged 3.2. On the block copolymer solution treated side of the abdomen, in 8 of the 20 surviving rats, some degree of adhesion was noted. The combined score, for the block copolymer treated areas including area and tenacity of adhesions in these 8 rats averaged only 1.63. These results taken with the results for the block copolymer treated side of the remaining 12 rats having no adhesions provided a combined average score of only 0.7. This difference is considered statistically significant at the p less than 0.005 level.

EXAMPLES 24–46

The procedure of Examples 2–23 is repeated utilizing a 20% by weight aqueous solution of a polyoxybutylene-based block copolymer having the structure generically shown as formula III and having a polyoxybutylene hydrophobe base having an average molecular weight of 3000 and a total average molecular weight of 10,000. Substantially similar results are obtained following the test procedure of Examples 2–23.

EXAMPLES 47–69

Utilizing a 30% by weight aqueous solution of a polyoxyethylene-polyoxypropylene block copolymer having the structure generically shown in formula I and having a polyoxypropylene hydrophobe base molecular weight of 2000, a polyoxyethylene content of 70% by weight, and a total average molecular weight of 5000, the test procedure of Examples 2–23 is repeated to obtain substantially the same results.

EXAMPLES 70–92

The procedure of Examples 2–23 is repeated using a 30% by weight aqueous solution of a polyoxyethylene-polyoxypropylene block copolymer adduct of ethylenediamine having a hydrophobe molecular weight of 1500 and a total average molecular weight of 2500, said copolymer having a hydrophile content of 60% by weight and a total average molecular weight of 5500. Substantially similar results are obtained.

EXAMPLE 93

This Example formulation describes a composition of the invention characterized as iso-osmotic, sterile, and having a pH of 7.4±0.2. An aqueous solution was made of a polyoxyethylene-polyoxypropylene block copolymer having the structure generically shown above as Formula IV and having a polyoxypropylene hydrophobe base average molecular weight of about 4000, a total average molecular weight of about 11,500, and containing oxyethylene groups in the amount of about 70% by weight of the total weight of copolymer. This copolymer (Formula VI below) is sold under the trademark PLURONIC® F-127 (also known as Poloxamer 407) by the BASF Corporation, Parsippany, N.J. A solution in TRIS hydrochloride buffer was made by dissolving said polymer in cold (4° C.) buffer to give a concentration of 25% by weight in accordance with the cold process procedure described above for forming aqueous solutions. More specific solution procedures are described in "Artificial Skin I Preparation and Properties of PLURONIC F-127 Gels For Treatment of Burns", *Journal of Biomedical Material Research* 6, 527, 1972, incorporated herein by reference. The block copolymer has the formula:

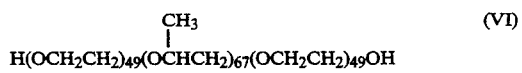

$$H(OCH_2CH_2)_{49}(OCHCH_2)_{67}(OCH_2CH_2)_{49}OH \quad (VI)$$
with CH₃ branch The formulation was sterilized by autoclaving at 121° C. and 15 psi for 15 minutes. The pH before autoclaving was found to be 7.3 and after autoclaving remained the same. The osmolality in the gelled state before autoclaving was determined to be 290±10 and after autoclaving 298±10 mOsm/kg. The gel strength (viscosity) in centipoise as measured at 37° C. using a Brookfield (spindle and cup) viscometer at 20 revolutions per minute was greater than 44,000 before autoclaving and greater than 44,000 after autoclaving. At 10 revolutions per minute, the viscosity was greater than 76,000 centipoise both before and after autoclaving.

EXAMPLES 94–115

The procedure of Examples 2–23 is repeated using the 25% by weight aqueous solution of Example 93. Substantially similar results are obtained.

EXAMPLE 116

The capped polyether polymer #2, described in U.S. Pat. No. 4,810,503, is mixed with surfactant #1, described in U.S. Pat. No. 4,810,503 in the proportions of Example #12 thereof to form an aqueous, ringing gel in a solution of TRIS hydrochloride buffer. The formulation is sterilized by autoclaving at 121° C. and 15 psi for 15 minutes. A sterile gel having a pH of about 7.2±0.2 is obtained which is further characterized as isotonic to mammalian body fluids.

EXAMPLES 117–138

The procedure of Examples 2–23 is repeated using the aqueous, isotonic gel of Example 116. Substantially similar results are obtained.

While this invention has been described with reference to certain specific embodiments, it will be recognized by those skilled in the art that many variations are possible without departing from the scope and spirit of the invention, and it will be understood that it is intended to cover all changes and modifications of the invention, disclosed herein for the purposes of illustration, which do not constitute departures from the spirit and scope of the invention.

The embodiments of the invention in which an exclusive property or privilege is claimed are defined as follows:

1. An isotonic aqueous composition for reducing post-surgical adhesion formation/reformation following injury to organs situated in mammalian body spaces, wherein said composition is a liquid at room temperature or below and a gel at mammalian body temperature, said composition consisting essentially of a polyoxyalkylene block copolymer of the formula

$$Y[(A)_n\text{—}E\text{—}H]_x \quad (I)$$

wherein A is a polyoxyalkylene moiety having an oxygen/carbon atom ratio of less than 0.5, x is at least 2, Y is derived from water or an organic compound containing x reactive hydrogen atoms, E is a polyoxyethylene moiety constituting at least about 60% by weight of the copolymer, n has a value such that the average molecular weight of A is at least about 500, as determined by the hydroxyl number of an intermediate of formula

$$Y[(A)_n\text{—}H]_x \quad (II)$$

and the total average molecular weight of the copolymer is at least about 5000; and a material selected from the group consisting of humectants, bactericides, bacteriostatic agents, and fibrinolytic agents.

2. The composition of claim 1, wherein Y is derived from a water soluble organic compound having 1 to about 6 carbon atoms and wherein said composition includes a pharmaceutically acceptable buffer sufficient to maintain the pH of said composition at about pH 7.4±0.2.

3. The composition of claim 2, wherein said polyoxyalkylene moiety is derived from an alkylene oxide selected from the group consisting of butylene oxide, propylene oxide, and mixtures thereof and Y is derived from an organic compound selected from the group consisting of propylene glycol, glycerin, pentaerythritol trimethylolpropane, ethylenediamine and mixtures thereof.

4. The composition of claim 3, wherein said aqueous composition contains a humectant which is present in the amount of about 0.5% to about 10% by weight of the total weight of the composition and is selected from the group consisting of propylene glycol, glycerin, sorbitol, and mixtures thereof.

5. The composition of claim 4, wherein said copolymer is a polyoxyethylene-polyoxypropylene block copolymer wherein said polyoxyethylene moiety constitutes at least about 70% by weight of the copolymer, the average molecular weight of A is at least about 1200, and the total molecular weight of the copolymer is at least about 5000.

6. The composition of claim 5, wherein the intermediate of Formula II is prepared by initiation with propylene glycol and has a molecular weight of at least about 1500, and said humectant is propylene glycol.

7. The composition of claim 6, wherein said copolymer has the formula:

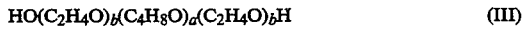

$$HO(C_2H_4O)_b(C_4H_8O)_a(C_2H_4O)_bH \qquad (III)$$

wherein a and b are integers such that the hydrophobe base represented by $(C_4H_8O)_a$ has a molecular weight of at least about 500 as determined by hydroxyl number, the polyoxyethylene chain constitutes at least about 70% by weight of the copolymer, and the copolymer has a total average molecular weight of at least about 5000; or
the formula:

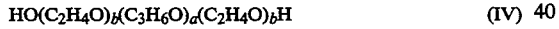

$$HO(C_2H_4O)_b(C_3H_6O)_a(C_2H_4O)_bH \qquad (IV)$$

wherein a and b are integers such that the hydrophobe base represented by $(C_3H_6O)_a$ has a molecular weight of at least about 900 as determined by hydroxyl number, the polyoxyethylene chain constitutes at least about 70% by weight of the copolymer, and the copolymer has a total average molecular weight of at least about 5000; or
the formula:

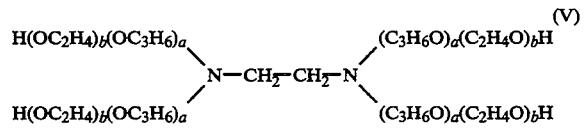

(V)

wherein a and b are integers such that the copolymer has a hydrophobe molecular weight of at least about 1500, a hydrophile content of at least about 70% by weight, and a total average molecular weight of at least about 5000.

8. The composition of claim 7, wherein said polyoxyalkylene block copolymer is

(VI)

present in the amount of about 10 to about 40% by weight of the total weight of said composition.

9. The composition of claim 7, wherein said polyoxyalkylene block copolymer is present in the amount of about 15% to about 30% by weight in said aqueous composition and said organs are situated in the peritoneal, pelvic, or pleural cavity.

10. A process for reducing post-surgical adhesion formation/reformation following injury to organs situated in mammalian body spaces comprising separating said organs from adjacent tissue with an effective amount of an isotonic aqueous composition consisting essentially of a surfactant and a polyoxyalkylene polyether wherein said composition is an aqueous gel at mammalian body temperature, said polyether having a molecular weight of about 10,000 to about 100,000 and selected from the group consisting of (A) polyoxyalkylene polyethers prepared by reacting ethylene oxide and at least one lower alkylene oxide having 3 to 4 carbon atoms with at least one active hydrogen-containing compound having from 3 to 10 carbon atoms and from 3 to 6 active hydrogens to prepare a heretic or block copolymer intermediate and further reacting said copolymer intermediate with at least one alpha-olefin oxide having an average carbon chain length of about 20 to about 45 aliphatic carbon atoms and wherein said alpha-olefin oxide is present in the amount of about 0.3 to 10 percent by weight based upon the total weight of said polyether, and (B) polyoxyalkylene polyethers prepared by reacting ethylene oxide with at least one active hydrogen-containing compound having from 2 to 10 carbon atoms and from 2 to 6 active hydrogens to prepare a homopolymer intermediate and further reacting said homopolymer intermediate with at least one alpha-olefin oxide having an average carbon chain length of about 20 to 45 aliphatic carbon atoms and wherein said alpha-olefin oxide is present in the amount of about 0.3 to 10 percent by weight based on the total weight of said polyether.

11. The process of claim 10, wherein said polyether is prepared using a heretic copolymer intermediate.

12. The process of claim 11, wherein said polyether is prepared using an alpha-olefin oxide having an average carbon chain length of about 20 to 30 carbon atoms, present in the amount of about 0.3 to 10 percent of the total weight of said polyether.

13. The process of claim 12, wherein said polyether contains a proportion of ethylene oxide residue to the residue of said lower alkylene oxide of 70 to about 90 percent by weight of ethylene oxide residue to about 30 to about 10 percent by weight of said lower alkylene oxide residue.

14. The process of claim 13, wherein said polyether is prepared using propylene oxide as the lower alkylene oxide.

15. The process of claim 10, wherein said polyether is prepared using a block copolymer intermediate.

16. The process of claim 15, wherein said polyether is prepared using an alpha-olefin oxide having an average carbon chain length of about 20 to 30 carbon atoms, present in the amount of about 0.3 to 10 percent of the total weight of said polyether.

17. The process of claim 16, wherein said polyether is prepared using a proportion of ethylene oxide residue to the residue of said lower alkylene oxide of from about 70 to about 90 percent by weight of ethylene oxide residue to about 30 to about 10 percent by weight of said lower alkylene oxide residue.

18. The process of claim 17, wherein said polyether is prepared using propylene oxide as the alkylene oxide.

19. The process of claim 10, wherein said polyether is polyether (B).

20. The process of claim 19, wherein said polyether is prepared using an alpha-olefin oxide having an average carbon chain length of about 20 to 30 carbon atoms, present in the amount of about 0.3 to 10 percent of the total weight of said polyether and said organs are situated in the peritoneal, pelvic, or pleural cavity.

21. An isotonic aqueous composition for reducing post-surgical adhesion formation/reformation following injury to tissues situated in mammalian body spaces, said composition forming a gel at room temperature or above, and consisting essentially of a surfactant and a polyether having a molecular weight of about 10,000 to about 100,000 and selected from the group consisting of
  (A) polyethers prepared by reacting ethylene oxide and at least one lower alkylene oxide having 3 to 4 carbon atoms with at least one active hydrogen-containing compound having from 3 to 10 carbon atoms and from 3 to 6 active hydrogens to prepare a heteric or block copolymer intermediate and further reacting said copolymer intermediate with at least one alpha-olefin oxide having an average carbon chain length of about 20 to about 45 aliphatic carbon atoms and wherein said alpha-olefin oxide is present in the amount of about 0.3 to 10 percent by weight based upon the total weight of said polyether, and
  (B) polyethers prepared by reacting ethylene oxide with at least one active hydrogen-containing compound having from 2 to 10 carbon atoms and from 2 to 6 active hydrogens to prepare a homopolymer intermediate and further reacting said homopolymer intermediate with at least one alpha-olefin oxide having an average carbon chain length of about 20 to 45 aliphatic carbon atoms and wherein said alpha-olefin oxide is present in the amount of about 0.3 to 10 percent by weight based on the total weight of said polyether.

22. The composition of claim 21, wherein said polyether is prepared using a heteric copolymer intermediate.

23. The composition of claim 22, wherein said polyether is prepared using an alpha-olefin oxide having an average carbon chain length of about 20 to 30 carbon atoms, present in the amount of about 0.3 to 10 percent of the total weight of said polyether.

24. The composition of claim 23, wherein the polyether is prepared using a proportion of ethylene oxide residue to the residue of said lower alkylene oxide of about 70 to about 90 percent by weight of ethylene oxide residue to about 30 to about 10 percent by weight of said lower alkylene oxide residue.

25. The composition of claim 24, wherein said polyether is prepared using propylene oxide as the lower alkylene oxide.

26. The composition of claim 21, wherein said polyether is prepared using a block copolymer intermediate.

27. The composition of claim 26, wherein said polyether is prepared using an alpha-olefin oxide having an average carbon chain length of about 20 to 30 carbon atoms, present in the amount of about 0.3 to 10 percent of the total weight of said polyether.

28. The composition of claim 27, wherein the polyether is prepared using a proportion of ethylene oxide residue to the residue of said lower alkylene oxide of about 70 to about 90 percent by weight of ethylene oxide residue to about 30 to about 10 percent by weight of said lower alkylene oxide residue.

29. The composition of claim 28, wherein polyether is prepared using propylene oxide as the lower alkylene oxide.

30. The composition of claim 21, wherein said polyether is polyether (B).

31. The composition of claim 30, wherein said polyether is prepared using an alpha-olefin oxide having an average carbon chain length of about 20 to 30 carbon atoms, present in the amount of about 0.3 to 10 percent of the total weight of said polyether, and said organs are situated in the peritoneal, pelvic, or pleural cavity.

* * * * *